(12) United States Patent
Hodgkinson et al.

(10) Patent No.: US 8,193,502 B2
(45) Date of Patent: Jun. 5, 2012

(54) OPTICAL ABSORPTION GAS SENSOR

(75) Inventors: Elizabeth Jane Hodgkinson, Bedfordshire (GB); John Robert Saffell, Cambridge (GB); Richard Smith, Essex (GB)

(73) Assignee: Alphasense Limited, Essex (GB)

( * ) Notice: Subject to any disclaimer, the term of this patent is extended or adjusted under 35 U.S.C. 154(b) by 0 days.

(21) Appl. No.: 12/052,916

(22) Filed: Mar. 21, 2008

(65) Prior Publication Data

US 2008/0239322 A1    Oct. 2, 2008

(30) Foreign Application Priority Data

Mar. 21, 2007    (GB) .................................. 0705356.4

(51) Int. Cl.
   *G01J 5/02*    (2006.01)
(52) U.S. Cl. ................ 250/339.12; 250/339.13; 250/343
(58) Field of Classification Search ............. 250/339.12, 250/339.13, 343–345
   See application file for complete search history.

(56) References Cited

U.S. PATENT DOCUMENTS

| | | | |
|---|---|---|---|
| 4,618,771 A | 10/1986 | Farren | |
| 5,850,354 A | 12/1998 | Bramley et al. | |
| 5,973,326 A * | 10/1999 | Parry et al. | 250/343 |
| 6,442,231 B1 * | 8/2002 | O'Hara | 378/45 |
| 6,762,410 B1 * | 7/2004 | Wiechers et al. | 250/343 |
| 2006/0226367 A1 * | 10/2006 | Hopkins et al. | 250/343 |
| 2008/0043470 A1 * | 2/2008 | Wimberly | 362/268 |
| 2008/0308733 A1 * | 12/2008 | Doncaster | 250/343 |

FOREIGN PATENT DOCUMENTS

| | | |
|---|---|---|
| GB | 2316172 | 2/1998 |
| GB | 2391310 | 2/2004 |
| GB | 2392721 | 3/2004 |
| GB | 2395260 | 5/2004 |
| WO | WO 98/10270 | 3/1998 |
| WO | WO 02/063283 | 8/2002 |
| WO | WO 03/102553 | 12/2003 |
| WO | WO 2004/042374 | 5/2004 |
| WO | WO 2004/051240 | 6/2004 |

OTHER PUBLICATIONS

Welford et al., "High Collection Nonimaging Optics", Academic Press, Inc.; pp. 54-63 and 204-208 (7 double pages), 1989.

(Continued)

*Primary Examiner* — David Porta
*Assistant Examiner* — Casey Bryant
(74) *Attorney, Agent, or Firm* — Nixon & Vanderhye PC (57) ABSTRACT

An optical absorption gas sensor comprising a body having an internal wall which defines a chamber, at least one aperture in the body through which a gas sample can enter the chamber, a light source, at least one reflector, a detector assembly which extends into the chamber and has a first side and an opposite second side, a detector which measures light which is incident at least a range of angles on at least a part of a first surface of the detector assembly on the first side of the detector assembly, wherein the light source is located within the chamber on the second side of the detector assembly, the whole being configured such that light from the light source passes through the gas sample and is reflected around the detector assembly, by the at least one reflector, onto the detector.

27 Claims, 3 Drawing Sheets

OTHER PUBLICATIONS

Sieber et al. "optical modeling of the analytical chamber of an IR gas sensor", Proc SPIE 4408, pp. 272-282, 2001.

Viola, "High-luminosity multipass cell for infrared imaging spectroscopy", Applied Optics, vol. 45 No. 12, pp. 2805-2809, 2006.

IRC-AI Carbon Dioxide Infrared Sensor, Pyroelectric Detector, pp. 1-3, (© ALPHASENSE Ltd), downloaded from and available in color at http://www.alphasense.com/pdf/NDIR_carbon_dioxide_IR.pdf.

* cited by examiner

OPTICAL ABSORPTION GAS SENSOR

This application claims priority to UK Patent Application No. 0705356A filed 21 Mar. 2007, the entire contents of which are hereby incorporated by reference.

FIELD OF THE INVENTION

The invention relates to the field of optical sensors, particularly optical absorption gas sensors.

BACKGROUND TO THE INVENTION

Optical absorption gas sensors determine the concentration of a gaseous analyte in a gas sample by measuring the attenuation of light passing through the gas sample due to absorption by the analyte of interest. Many such sensors use light in the infra-red region where gases such as carbon dioxide and methane have absorption lines.

In dispersive infra-red sensors, light of a series of wavelengths which includes one or more absorption lines of the analyte which is to be detected is directed through a gas sample and its intensity is measured by a detector. In non-dispersive infra-red (NDIR) sensors, light of a broad range of wavelengths is passed through a gas sample and the intensity of light in a selected wavelength band, which includes one or more absorption lines of the analyte of interest, is measured, typically using a band-pass filter and a light detector, such as a thermopile, photodiode or pyroelectric detector.

In optical absorption gas sensors, the concentration of the analyte gas can be established using the Beer-Lambert Law; $I_f = I_o 10^{-\alpha L c}$ where $I_o$ is the intensity of light that is incident on a gas sample, $I_f$ is the intensity of light after passing through the material, L is the distance that the light travels through the material from the source to the detector (the path length), c is the concentration of the analyte in the material, and $\alpha$ is the absorption coefficient of the analyte species. The Beer-Lambert law applies to monochromatic radiation and the corresponding relationship for polychromatic light can be established by summation/integration. In some optical absorption sensors, light reaching the detector will have components with a range of path lengths, and so there is usually some apparent deviation in practice from the theoretical predictions of the Beer-Lambert Law which can be determined from the geometry of the sensor and empirical measurements.

Many optical absorption gas sensors measure the intensity of light which has passed through the gas sample at two different wavelength bands, one of which includes absorption lines of the analyte, and one of which does not and so functions as a reference. For example, in an NDIR sensor, it is known to use a single light detector which can measure light at two different wavelengths, perhaps using a variable-wavelength Fabry-Perot interferometer, or to use separate measurement and reference light detectors, each of which has a different wavelength band-pass filter.

In order to improve the precision and sensitivity of optical absorption gas sensors, it is desirable to maximise the path length of the light which falls on the detector and therefore increase the total absorption due to a given concentration of analyte. For example, U.S. Pat. No. 4,618,771 (Beckman Industrial Corporation) and U.S. Pat. No. 5,850,354 (Vaisala Oy) disclose elongate analysers in which the path length is maximised by using a long and relatively thin measurement chamber.

However, there are many industrial applications where it is desirable to minimise the size of a sensor. This may be to reduce bulk, or to improve the speed of response of the sensor, by minimising the volume of the measurement chamber and therefore the amount of time required to introduce a gas sample to the measurement chamber whether actively (e.g. using a pump) or passively by diffusion. A number of solutions have been proposed in the art for maximising the path length for a given size of sensor. Typically, these solutions provide sensors in which light from an appropriate source is reflected many times through the gas sample before it reaches the detector. Examples of sensors of this type are disclosed in GB 2,391,310A (Edinburgh Instruments Limited), GB 2,395,260 A (e2v Technologies Limited), and WO 02/063283 (Dynament Limited).

A disadvantage of sensors in which light is reflected many times is that small manufacturing errors can have a significant adverse effect on the amount of light reaching the detector. Imperfections may amplify variations in the amount of light which reaches the detector due to variations in the intensity or exact position of the light source in use. These problems are particularly acute for sensors which comprise separate measurement and reference light detectors. In this case, errors which affect the relative amount of light which reaches the measurement and reference light detectors, or which affect the relative distribution of path lengths of light reaching the measurement and reference detectors, are of particular concern. Therefore, an important design parameter, which is taken into account in the present invention, is the tolerance of the sensor to manufacturing imperfections and variations in the intensity, spectral properties and/or path of light in use.

These issues are particularly critical in sensors which must occupy small volumes. For example, in the gas sensing industry, there is a standard gas sensor configuration, which takes the form of a cylinder with a 20 mm diameter, and a height of 16.6 mm. This is a confined volume which presents a significant engineering challenge. Furthermore, commonly packaged light-emitting devices and detectors are of a size which can become a significant proportion of the volume of the sample chamber in smaller sensors.

Some aspects of the present invention aim to provide an optical absorption gas sensor which balances the above factors to provide a good performance relative to other sensors of similar size and manufacturing cost.

SUMMARY OF THE INVENTION

According to a first aspect of the present invention there is provided an optical absorption gas sensor comprising a body having an internal wall which defines a chamber, at least one aperture in the body through which a gas sample can enter the chamber, a light source, at least one reflector, and a detector assembly which has a first side and an opposite second side, a detector which measures light which is incident at at least a range of angles on at least a part of a first surface of the detector assembly on the first side of the detector assembly, characterised in that the detector assembly extends into the chamber and the light source is located within the chamber on the second side of the detector assembly, the whole being configured such that light from the light source passes through the gas sample and is reflected around the detector assembly, by the at least one reflector, onto the detector.

Within this specification and the appended claims, the term "light source" refers to the region of the sensor which emits photons in use, for example, the incandescent part of the filament of an incandescent bulb, the light-emitting semiconductor junction of a light-emitting diode, or the volume of a fluorescent lamp or a high-intensity discharge lamp which emits light in use. Typically, the light source will be part of a light-emitting device such as an incandescent bulb, light-emitting diode, fluorescent lamp, high-intensity discharge lamp, or planar plasmon source.

Within this specification and the appended claims, "located within the chamber on the second side of the detector assembly" includes both the possibility that the light source is part of a light-emitting device which is attached to, in contact with, or an integral part of, the second surface of the detector assembly, on the second side of the detector assembly, and also the possibility that the light source is part of a light-emitting device which is not attached to or in contact with the detector assembly, but is spaced apart from the detector assembly, on the second side thereof.

With this specification and the appended claims, the term "opposite second side" is not intended to imply a limitation as to the orientation of surfaces on either side of the detector, or that the surfaces on either side of the detector are not a single continuous surface, e.g. opposite curved faces of a cylinder.

Preferably, there is no direct light path from the light source to the detector and all light must pass around the detector assembly. Preferably, there is no light path from the light source to the detector, such that light is incident on the detector at an angle at which it will be measured, in which the light has been reflected less than twice by the at least one reflector.

The detector may measure light which falls onto the first surface of the detector at an angle which is generally parallel to a line extending from the detector to the light source. Accordingly, as light is reflected around the detector assembly, light will generally require to have been reflected more than once to have an orientation which is generally parallel to a line extending from the detector to the light source. The detector and the light source may be directly opposite each other on opposite sides of the detector assembly. It may be that the light source is attached to the second surface of the detector assembly and that the first and second surfaces of the detector assembly are generally parallel.

The detector typically measures light which is incident on at least a part of the first surface of the detector assembly at a finite range of angles. The detector may be in the form of an integrated device which has a first planar surface which forms the first surface of the detector assembly and which is adapted to measure light which falls onto one or more detection regions of the planar surface, normal to the planar surface and at a range of angles around the normal to the planar surface. Typically, the integrated device has a second planar surface which is parallel to the first planar surface. The light source is preferably behind the detector, i.e. located within a volume defined by a prism which has the same cross-section as the first planar surface of the integrated device and which extends from the second side of the integrated device perpendicular to the first planar surface of the integrated device. The integrated device may have a body in the form of a disc (preferably, a right circular cylinder) and the first planar surface is typically one of the end faces of the disc. Where applicable, the second planar surface is typically the opposite end face of the disc. The detector assembly may comprise a support for a disc-shaped detector.

The detector assembly may extend from the internal wall into the chamber. The detector assembly may have a major dimension which extends from the internal wall towards a central axis of the chamber and the planar surface of the detector may be parallel to the major dimension of the detector assembly. It may be that light is reflected around only one side of the detector assembly.

Preferably, at least one reflector is located on the internal wall. Typically, at least a first reflector and a second reflector are located on the internal wall and the majority of the light from the light source is reflected by both the first and second reflectors before it is incident on the detector. The term "second reflector" is not intended to imply that there are not one or more additional reflectors, other than the first and second reflectors, which reflect light after it has been reflected by the first reflector and before it is reflected by the second reflector. However, in some embodiments of the invention, the majority of the light from the light source which is measured by the detector has reflected only off the first and second reflectors after it has been emitted by the light source, and optionally reflected by the collector (see below), where present. Typically, the majority of the light from the light source which is measured by the detector has reflected only once of each of the first and second reflectors.

Preferably, a collector (see below) is provided to direct the majority of the light from the light source (preferably at least 60% of the light from the light source) onto the first reflector. The first reflector may be configured to direct the majority of received light from the light source onto the second reflector. The second reflector may be configured to direct at least 40%, and preferably the majority of light received from the first reflector (and optionally one or more additional reflectors) onto the detector.

The light which falls onto the first reflector may be divergent. The light which falls onto the second reflector may be less divergent than the light which falls onto the first reflector. The second reflector may be concave and configured such that light reflected from the second reflector is less divergent than the light which is incident on the second reflector and that light falling on the detector is predominantly convergent. Where a reflector is located on a curved wall, the reflector may have a different radius of curvature to the curved wall, for example a shorter radius of curvature.

Typically, the chamber has a generally circular cross-section. The body of the sensor may be generally cylindrical (typically a right circular cylinder) and the chamber may be generally cylindrical (typically a right circular cylinder). The diameter of the cylindrical body may be greater than the axial length of the cylindrical body. The body of the sensor may correspond in dimensions to a recognised standard size; for example the body of the sensor may have an external diameter of 20 mm±0.2 mm (preferably 20 mm) and a length of 16.6 mm±0.2 mm (preferably 16.6 mm).

Where the chamber has a generally circular cross-section, the path of the majority of the light from the light source to the detector via the first and second reflectors preferably passes around the centre of the circle.

Preferably, the detector is in the form of a generally flat body (such as a disc) which extends obliquely from the inner wall of the body of the sensor into the chamber (i.e. not radially when the chamber is generally circular, nor directly towards the centre of the chamber where the chamber is not circular) such that the volume within the chamber on the first side of the detector is less than the volume within the chamber on the second side of the detector. In combination with the use of two or more reflectors which reduce the divergence of the light beam, and which are configured such that light falling on the detector is predominantly convergent, this allows a collector (see below) with a larger internal reflective surface area to be provided than would be the case if the planar detector extended inwards along a radius of the chamber and bisected part of the chamber. This allows a larger collector to be provided which better controls the spatial and angular distribution of light from the light-source which is directed onto the first reflector.

The light source is typically the light-emitting part of a light-emitting device. The light emitting device may comprise a light-emitting diode, fluorescent lamp, high-intensity discharge lamp, planar plasmon source, or, preferably, an incandescent lamp, in which case the light source is the filament of the incandescent lamp. Typically, the light source will emit light omnidirectionally. Typically, the light source emits infra-red light, which may be near and mid infra-red light, by which we mean light with a wavelength of between 0.75 and 5 microns. The light-emitting device will be selected to emit light of the desired wavelength range. The light-emitting device may also emit light of a wavelength which is not used for measurement purpose. For example, incandescent lamps which emit infra-red light typically also emit visible light.

The sensor may further comprise a collector, located within the chamber, which has an interior reflective surface which directs light from the light source onto the first reflector through an output aperture of the collector. The collector may reflect some, or preferably the majority, of light which is emitted by the light source in a direction other than directly onto the first reflector, such as to direct the said light onto the first reflector. The collector may be located on one side of the light source, but preferably the light source is within the interior of the collector.

At least part of the collector may comprise a wall having an interior reflective surface which takes the form of a part of a conic section rotated around an axis of rotation extending from the light source to the first reflector. The axis of rotation may be the axis of the conic section and the interior reflective surface of the collector may be in the form of a paraboloid. Preferably, the axis of rotation may be different to the axis of the conic section and, more preferably, the interior reflective surface of the collector may be in the form of a compound parabolic collector, or a compound parabolic collector which is partially truncated at the output aperture.

The light-reflecting interior wall of a portion of the collector preferably comprises a portion of the interior of a sphere and the light source is typically located close to, or preferably intersecting, the centre of the sphere portion (i.e. the point which would be the centre of the sphere if it were a complete sphere). Preferably, the part-spherical portion comprises all, or typically the majority of a hemisphere. The part-spherical portion may fill the input angle of the compound parabolic collector.

This has the effect that, to a first order of approximation, light which is emitted by the light source in the region of the centre of the part-spherical portion, will be reflected by the portion of the interior of a sphere and the reflected light will form a mirror image of the light source. This reduces the sensitivity of the amount of light falling on the detector to the precise location of the light source. This increases tolerance to manufacturing imperfections, particularly those imperfections resulting in the light source not being coincident with the centre of the sphere portion, and also increases tolerance to movement of the light source in use. This is particularly relevant where the light source is the filament of an incandescent lamp which may move in use due to thermal expansion, vibration, shocks etc. This is especially relevant in embodiments of the sensor in which the optics are symmetric about a plane of symmetry, which is discussed further below. The use of a sphere portion is especially beneficial when the size of the light source is significant compared to the size of the collector, e.g. where the light source extends across more than 10% of the width of the collector in a plane which bifurcates the light source.

The light-source may be part of a light-emitting device which extends into the collector, through an aperture in the interior reflective surface of the collector. Where the collector comprises a wall having an interior reflective surface which takes the form of a part of a conic section rotated around an axis of rotation extending from the light source to the first reflector, the light-emitting device preferably extends into the collector such that the light-emitting portion is close to, and preferably intersects, the axis of rotation of the interior surface of the collector. The light-emitting device may be elongate, for example the light-emitting device may be an elongate light-emitting diode, incandescent bulb, or fluorescent lamp.

The light-emitting device may extend into the collector other than parallel to the axis of the collector. Preferably, the light-emitting device extends into the collector through an aperture in the interior reflective surface of the collector in a direction towards the rear of the collector (i.e. away from the output aperture of the collector).

This allows the light source to be located further from the first reflector than would be the case if the light-emitting device extended into the collector towards the first reflector. This increases the average path length from the light source to the detector.

Preferably, the light-emitting device is supported by the detector assembly, on the second side of the detector assembly, and extends into the collector through an aperture in the interior reflective surface of the collector towards the rear of the collector.

The light-emitting device may extend orthogonally to the major dimension of the detector assembly. Where the detector assembly comprises a planar detector having parallel first and second surfaces, which detects light which is incident on the first surface of the planar detector, in a direction which is normal to the first surface or at a range of angles around the normal to the first surface, the light-emitting device may extend from the second surface of the detector assembly parallel to the normal of the first and second surfaces of the detector. Alternatively, the light-emitting device may extend from the second surface of the detector assembly at an angle to the normal of the first and second surfaces of the detector.

The light-source may be elongate, for example, the light-source may be an elongate filament of an incandescent bulb. The elongate light-source may be parallel to the length of the light-emitting device. The elongate light-source may be orthogonal to the length of the light-emitting device. The elongate light-source may be other than parallel to the axis of the collector. In embodiments with a plane of symmetry (discussed below) the elongate light-source may be other than symmetric about the plane of symmetry. This will occur if, as is common with the filament of incandescent bulbs, the filament is orthogonal to the length of the incandescent bulb and the incandescent bulb extends into the collector towards the rear of the collector. In this case, where the interior surface of the collector comprises part of the interior surface of a sphere, this has the effect of, to a first order of approximation, avoiding an asymmetry in the distribution of light about the plane of symmetry.

Typically, the body comprises a plurality of apertures through which a gas sample can diffuse into the chamber. Where the body of the sensor is generally cylindrical, the plurality of apertures is typically located on an end face of the generally cylindrical body. Preferably, light is reflected around the axis of the cylinder from reflectors located on the cylindrical inner wall of the cylinder.

The detector may be capable of measuring light at both a measurement wavelength band and a separate reference wavelength band. For example, the detector may comprise a variable-frequency Fabry-Perot interferometer. The detector may comprise a beam-splitter which directs received light onto reference and measurement detectors through respective reference and measurement filters.

Where the analyte is methane, the detector will typically measure absorption of light between 3.2 and 3.5 microns wavelength. Where the analyte is carbon dioxide, the detector will typically measure absorption of light between 4.2 and 4.4 microns wavelength. Where the analyte is carbon monoxide, the detector will typically measure absorption of light between 4.5 and 4.9 microns wavelength. Where the analyte is dinitrogen oxide, the detector will typically measure absorption of light between 4.4 and 4.7 microns wavelength. Where the analyte is nitrogen monoxide, the detector will typically measure absorption of light between 5.1 and 5.7 microns wavelength.

The detector may comprise separate measurement and reference detectors which measure light of different wavelength bands which fall onto different locations on the detector. For example, where the detector has a planar first surface, the measurement and reference detectors may be at different locations on the planar first surface. The measurement and reference detectors may comprise distinct devices which are independently attached to the detector assembly. The separate measurement and reference detectors may each comprise filters with different pass-bands.

Preferably, the distribution of light within the chamber is symmetric about a plane of symmetry which passes through the light source and the detector. More preferably, the chamber is generally cylindrical and the plane of symmetry is orthogonal to the axis of the cylinder. Preferably, the reflectors are located on the curved inner walls of the cylinder and at least 90% of light is reflected only off reflectors located on the curved inner walls of the cylinder and not reflected off the inner end faces of the cylinder. The inner end faces may be substantially non-reflective.

Preferably, the measurement and reference detectors are located symmetrically on either side of the plane of symmetry. Thus, the amount of light and the distribution of path length (and thus the variation in attenuation with analyte concentration of the light) which falls on the measurement and reference detectors is the same. Where the detector has a planar first surface, the plane of symmetry will typically be orthogonal to the planar first surface of the detector. Typically, the plane of symmetry will bisect the planar first surface of the detector.

Preferably, the light source is centred on the plane of symmetry. Preferably, the light source is part of an elongate light-emitting device which extends into the collector in the plane of symmetry. Where the light-emitting device extends into the collector through an aperture in the reflective inner surface of the collector, this has the effect of distorting the pattern of reflection of light in comparison to an uninterrupted collector. However, where the measurement and reference detectors are located symmetrically on either side of the plane of symmetry and the light-emitting device extends into the collector in the plane of symmetry, the distortion does not affect the relative amount of light which reaches the measurement and reference detectors, nor the average path length of light which reaches the measurement and reference detectors. In this case, the light-emitting device will typically be symmetrical on either side of the plane of symmetry.

Either or both of the first and second reflectors are preferably concave in a plane which is orthogonal to the plane of symmetry and symmetric about the plane of symmetry. The collector and the first reflector are preferably configured such that the distribution of light reflected from the surface of the first reflector is bifurcated. Where the detector comprises separate measurement and reference detectors located symmetrically on either side of the plane of symmetry, the collector and reflectors are preferably configured such that the distribution of light which reaches the detector is bifurcated so that the intensity of light which falls on each of the measurement and reference detectors is greater than the intensity of light which is incident on the detector in the plane of symmetry between the measurement and reference electrodes. This enables a larger proportion of the light from the light source to reach the measurement and reference detectors than would be the case if the distribution of light which reaches the detectors was more intense in the plane of symmetry than at each of the measurement and reference detectors.

The invention also extends in a second aspect to an optical sensor comprising a light-emitting device including a light source, for use in generating light for the purposes of carrying out a measurement, and a collector having a reflective inner surface and an axis, wherein the light-emitting device extends into the collector through an aperture in the collector, other than parallel to the axis of the collector.

This optical arrangement is useful for sensors where it is necessary to make a measurement in a confined space. In particular, the light-emitting device may extend into the collector in a generally rearwards direction where the light-emitting device is elongate, having a base and a tip at the opposite end to the base, and the light source is more than 50% of the distance from the base of the light-emitting device to the tip, this enables the light source to be located further back in the collector than would be the case if the light-emitting device extended into the collector from the rear of the collector, along the axis of the collector. Preferably, the light source is located on the axis of the collector. The collector may correspond to the collector discussed in relation to the first aspect of the invention.

The light generated by the light source may be directed onto a detector, optionally after interaction with one or more optical components. However, the light may have other roles in the detection procedure. For example, the light generated by the light source might be used to stimulate fluorescence which is detected by alternative means.

Other optional and preferred features of the light source and collector correspond to those discussed in relation to the first aspect of the invention. Preferably, the optical sensor is an optical absorption gas sensor. The optical sensor may be an optical absorption gas sensor according to the first aspect of the present invention.

According to a third aspect of the present invention, there is provided an optical sensor comprising a light-emitting device which includes a light source, for use in generating light for the purpose of carrying out a measurement, and a collector which has a reflective inner surface disposed around the light source and an output aperture, wherein the collector comprises a part-spherical portion located on the side of the light source which is opposite to the output aperture, and the light source comprises the light-emitting part of a luminescent filament.

Preferably, the filament is part of an incandescent lamp.

The filament may be elongate and orientated such that it is neither parallel to, nor orthogonal to, the axis of the collector. Typically, the light-emitting device extends into the collector through an aperture in the collector, in a direction other than parallel to the axis of the collector.

Preferably, the radius of the part-spherical portion is less than ten times, five times, or more preferably less than three times the length of the light-emitting part of a luminescent filament.

Preferably, the optical sensor is an optical absorption gas sensor. Other optional and preferred features correspond to those discussed in relation to the first and second aspects of the invention.

According to a fourth aspect of the present invention, there is provided an optical absorption gas sensor comprising a light source and a detector for measuring light from the light source which has passed through a gas sample so that the concentration of an analyte gas can be established from the absorption of light by the analyte gas, wherein the sensor further comprises a collector having a reflective inner surface, at least a portion of which is in the shape of at least a portion of a compound parabolic collector or offset paraboloid.

Other optional and preferred features correspond to those discussed in relation to the first, second and third aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
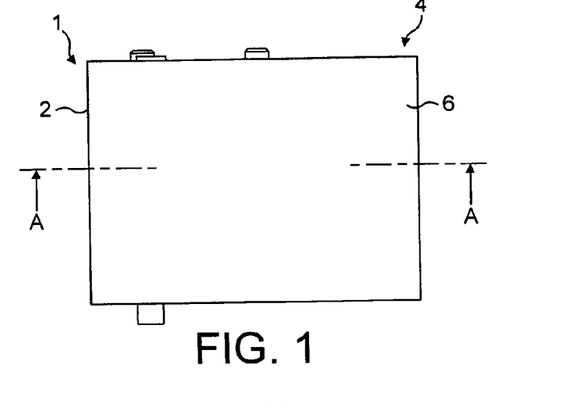
FIG. 1 is a side view of a generally cylindrical optical absorption gas sensor.
Figure 2:
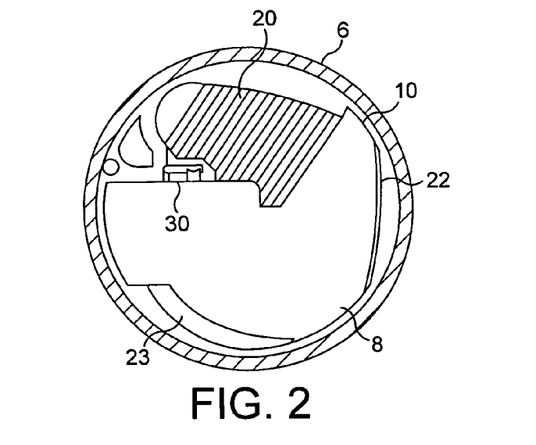
FIG. 2 is a cross-section of the gas sensor through the plane A-A viewed in an upwards direction, omitting the incandescent bulb, and the detector assembly (including the detector)
Figure 3:
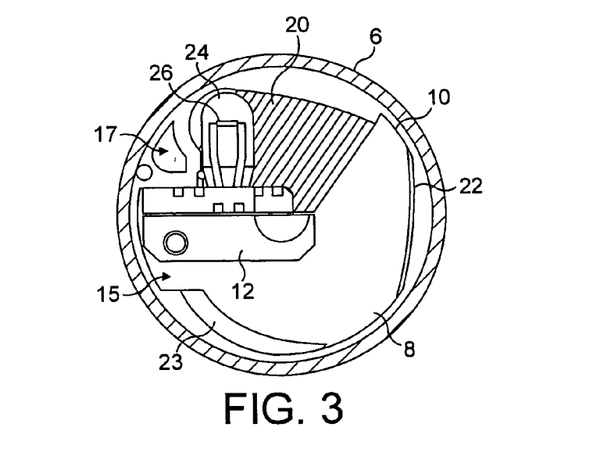
FIG. 3 is a cross-section of the gas sensor through the plane A-A viewed in an upwards direction, including the incandescent bulb and the majority of the detector assembly, but excluding the detector.
Figure 4:
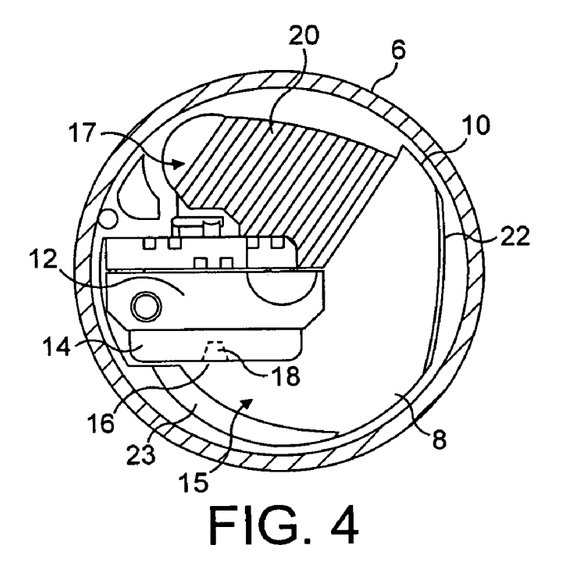
FIG. 4 is a cross-section of the gas sensor through the plane A-A viewed in an upwards direction, omitting the incandescent bulb.
Figure 5:
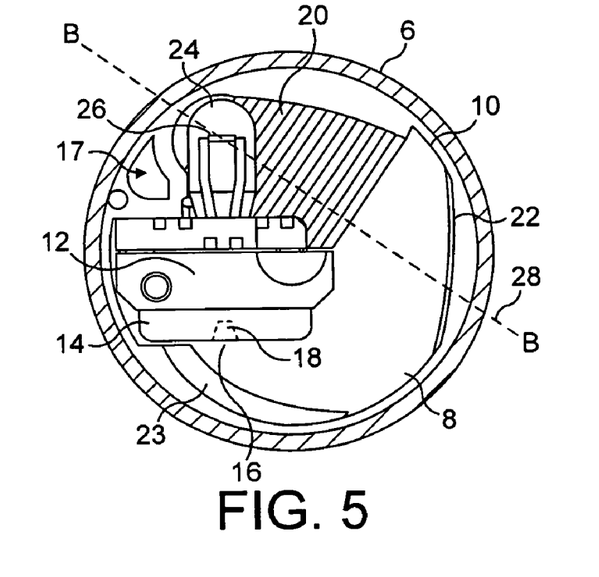
FIG. 5 is a cross-section of the gas sensor through the plane A-A viewed in an upwards direction.

FIG. 1 is a side view of an optical absorption gas sensor 1 having a body 2, which is generally in the shape of a right circular cylinder, a top surface 4 and cylindrical outer wall 6. FIG. 2 is a cross-section of the sensor through plane A-A viewed in an upwards direction, omitting the detector assembly (including the detector) and the incandescent lamp. FIG. 3 is a corresponding cross-section, omitting only the detector. FIG. 4 is a corresponding cross-section, omitting the incandescent lamp, and FIG. 5 is a corresponding cross-section which includes all components.

The sensor comprises an internal chamber 8 (which is also generally in the form of a right circular cylinder), defined by the inner wall 10 of the sensor body. A detector assembly 12 extends from the inner wall of the sensor into the chamber and supports a detector 14 in the form of a disc with a planar first surface 16, which is attached to a first side of the detector assembly. The detector assembly and sensor body are each formed from a plastics material and the interior of the sensor body is coated with a reflective material, such as a gold layer.

Measurement and reference detectors 18 are located symmetrically above and below plane A-A. The measurements and reference detectors are each adapted to measure the intensity of light of a predetermined wavelength range which is incident on the respective detector, either normal to the first surface of the detector, or within a range of angles of the normal.

An infra-red incandescent lamp (not shown in FIG. 2 or 4), is provided on the opposite, second side of the detector assembly. The infra-red incandescent bulb functions as a light-emitting device, and includes a filament which functions as the light source, emitting near infra-red light with a broad range of wavelengths. The light-emitting device extends from the detector assembly into a collector 20 which has a reflective inner surface for directing light emitted by light source across a portion of the chamber onto a first reflector 22. The filament of the light-emitting device is located at the focus of the collector. The collector is configured to direct the majority of light from the light source onto a first reflector. Light which is incident on the first reflector is predominantly reflected onto the second reflector, which reflects a proportion of incident light onto the detector. As the detector is located on a first side 15 of the detector assembly and the light source is located within the chamber on the opposite second side 17 of the detector assembly, light passes through the gas sample in use, and is reflected around the detector assembly, by the at least one reflector, onto the detector.

In cross-section through plane A-A, the first reflector 22 is parabolic, or alternatively circular, with a radius of curvature which is greater than the radius of curvature of the generally circular chamber. In the same plane, the second reflector 23 is in the form of a section of an offset parabola. The first and second reflectors are biconic and are concave in vertical cross-section. The first and second reflectors are protrusions from the inner wall of the sensor.

FIGS. 3 and 5 show the location of the incandescent bulb 24 and its filament 26 which, as closely as possible, intersects the axis of the collector 28, but is at an acute angle to the axis of the collector. FIG. 2 illustrates the aperture 30, through which the incandescent bulb extends into the collector.

Figure 6:
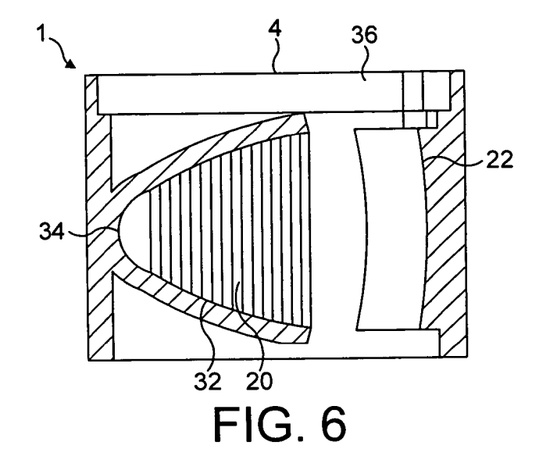
FIG. 6 is a cross-section of the gas sensor through plane B-B of FIG. 5.

FIG. 6 is a cross-section through the sensor in the plane B-B (see FIG. 5) which is orthogonal to plane A-A and includes the axis 28 of the collector. The inner reflective surface of the collector comprises a partially truncated compound parabolic reflector 32 and a part-hemispherical surface 34, which is located behind the filament of the incandescent lamp (i.e. on the side of the filament which is opposite the first reflector), with the filament intersecting the centre of the part-sphere as closely as possible given manufacturing tolerances. Compound parabolic collectors/concentrators are discussed in High Collection Nonimaging Optics (Welford, W. T. and Winston, R., published by Academic Press, Inc., 1989), from p. 205. FIG. 6 also illustrates a gas permeable, light resistant screen 36, located underneath the top surface of the sensor 4 for minimising the ingress of light into the measurement chamber, whilst allowing a gas sample to diffuse into the measurement chamber via one or more apertures in top surface of the sensor body and the screen.

Figure 7:
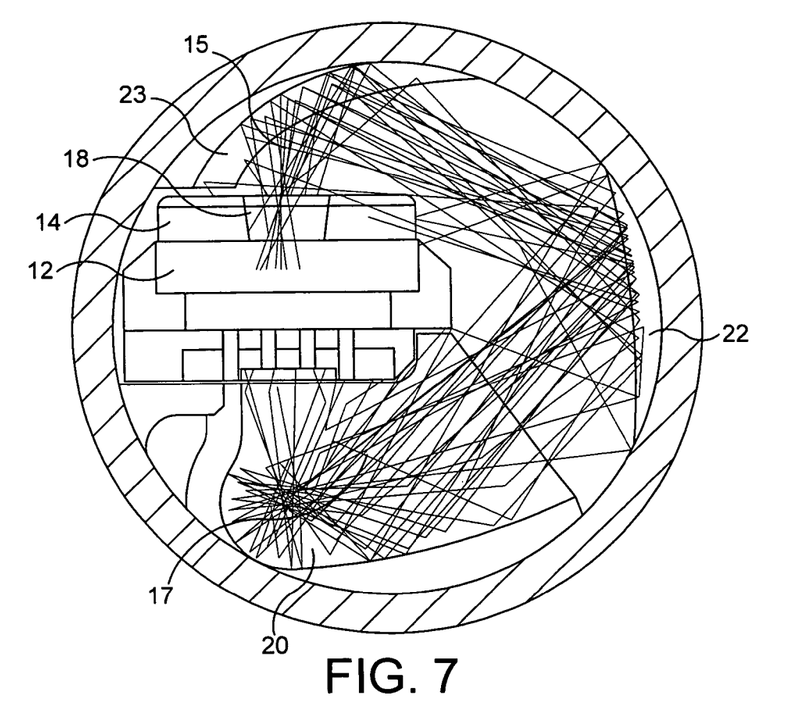
FIG. 7 is a cross-section of the gas sensor through plane A-A, viewed in a downwards direction, illustrating ray traces from the filament to the detector.

FIG. 7 is a cross-section through plane A-A illustrating ray traces from the filament to the detector. Light which is emitted by the filament of the incandescent bulb is generally omnidirectional. A proportion of the light emitted from the filament is incident directly onto the first reflector. Other light is reflected from the offset parabolic section of the inner surface of the collector and/or the part hemispherical section of the inner wall of the collector. The resulting divergent beam of light is incident predominantly on the first reflector, although a proportion will reflect off other parts of the reflective internal wall of the sensor. Light which is incident on the first reflector is then predominantly reflected onto the second reflector, which causes the beam to converge onto the measurement and reference detectors.

The distribution of light is symmetric about plane A-A. As the first and second reflectors are concave in a vertical plane, they reduce the vertical divergence of the light which is received from the filament and collector. The combination of the offset parabolic collector and the biconic first reflector has the effect that the light which is incident on the second reflector, and on the first surface of the detector, is bifurcated, such that the intensity of light falling on the measurement and reference detectors is greater than the intensity of the light which falls on the first surface of the detector in plane A-A.

The measurement and reference detectors each comprise a band pass filter and a light intensity measurement device, such as a thermopile, photodiode or pyroelectric detector. The filter on the measurement detector is selected so that the wavelength range of the light which is measured by the measurement detector includes absorption lines of the analyte of interest, which may for example be carbon dioxide or methane. The wavelength range of the band pass filter on the reference detector is selected so that the light which is measured by the reference detector is independent of the concentration of analyte within the measurement chamber. Where possible, the wavelength range of light detected by the reference detector is selected to be independent of the concentration of gases which may interfere with the reading, such as water. The concentration of the analyte gas within the measurement chamber can be determined from the signals produced by the measurement and reference detectors and the Beer-Lambert law or predetermined calibration data.

The sensor can be conveniently manufactured using a plastic moulding which is coated on the inner surface with a reflective material, such as gold. The detector assembly may include a printed circuit board which supports the detector, or a plastic moulding into which the detector and incandescent lamp fit.

The same sensor construction can be used for sensors to detect any of a range of gaseous analytes, such as carbon dioxide or methane, by selecting band pass filters which are appropriate to the analyte gas. The sensor may conform to an industry standard configuration. For example, the sensor may have an external diameter of around 20 mm and a height of around 16.6 mm.

The exemplary sensor is advantageous for several reasons:
a) The location of the light source on the opposite side of the detector assembly to the light sensitive side of the detector and the use of reflectors to reflect light around the periphery of the detector assembly maximises the available path length in a confined volume. Where the gas sensor is in the form of a cylinder with a diameter of around 20 mm and a height of around 16.6 mm, the path length from the light source to the detector is predominantly between 2 cm and 3 cm. This is a large path length given the use of only two reflections and a moderate variation in path length.
b) The introduction of the incandescent bulb into the collector in a generally rearwards direction enables the filament to be located further back within the collector than would be the case if the incandescent bulb was fitted so that it extended from the base of the collector, parallel to the axis of the collector. This increases the overall path length, and reduces the variation in the path length of light received at the detectors, by minimising the difference in path length between light which was emitted directly towards the first reflector along the axis of the collector and light which was emitted directly backwards, along the axis of the collector to the rear of the collector before being reflected towards the first reflector. This also increases the optical efficiency of the collector.
c) By using a collector with part-hemispherical rear portion, the pattern of light directed onto the first reflector is broadly symmetric, which would not otherwise be the case given the orientation of the filament of the incandescent lamp. This minimises error in the measured analyte concentration resulting from movement of the filament due to, e.g. vibration or thermal expansion in use.
d) The use of a second reflector which reduces the divergence of the light which is incident on it, and directs it onto the detector, allows a strongly divergent beam of light to be used. By using a divergent beam, rather than a collimated beam, we have increased the total proportion of light from the light source which reaches the detector.
e) The light-sensitive first surface of the detector does not extend directly from the periphery of the sensor in a radial direction towards the centre of the sensor, but extends at an oblique angle. Thus, the volume of the sensor on the side of the detector assembly which includes the detector (the first side) is larger than the opposite second side. This has allowed the construction of a larger collector, with better optical properties, in a confined space and has facilitated the maximisation of the overall path length.
f) The use of a compound parabolic collector is advantageous as it allows collection of light over a wide angular range and produces an emergent cone of defined divergence and cross-section. In practice, the compound parabolic collector is typically partially truncated at the output aperture due to space constraints.
g) The combination of the compound offset parabolic collector and the biconic first reflector has produced a bifurcated light distribution, enhancing the proportion of light which is incident on the measurement and reference detectors at an angle where it can be detected. This is surprising, because it is counterintuitive that the combination of a compound parabolic collector and a biconic first reflector would produce this effect.
h) As the majority of light is only reflected twice, other than reflections within the collector, the design is tolerant of manufacturing errors. The broad emergent cone of light from the collector and the wide angular range of light from the collector means that imperfections on the surfaces of the first and second reflectors have minimal impact on the accuracy of measurements carried out using the sensor.
i) By directing light generally around the circular periphery of the cylindrical sensor, rather than reflecting light from the inside of the circular top face of the sensor, the detector optics are not responsive to any light which penetrates the light-resistant layer. The optical arrangement also permits the use of non-reflective materials in the top and bottom faces of the cylinder, and allows greater manufacturing freedom, for example it enables the construction of electronic circuits at the bottom of the device and gas-permeable screens at the top.

Additional benefits of the invention are apparent to one skilled in the art from the disclosure herein. Further variations and modifications can be made within the scope of the invention which is disclosed herein.

What is claimed is:

1. An optical absorption gas sensor comprising a body having an internal wall which defines a chamber, at least one aperture in the body through which a gas sample can enter the chamber, a light source, at least one reflector, a detector assembly which extends into the chamber and has a first side and an opposite second side and which includes a detector on one face of the detector assembly which measures light which is incident at least a range of angles on at least a part of a first surface of the detector assembly on the first side of the detector assembly, wherein the light source is located within the chamber on an opposite face of the detector assembly on the second side of the detector assembly, the gas sensor being configured such that light from the light source passes through the gas sample and is reflected around the detector assembly, by the at least one reflector, onto the detector.

2. An optical absorption gas sensor according to claim 1, wherein there is no light path from the light source to the detector, such that light is incident on the detector at an angle at which it will be measured, in which the light has been reflected less than twice by the at least one reflector.

3. An optical absorption gas sensor according to claim 1, wherein the detector measures light which falls onto a first surface of the detector at an angle which is generally parallel to a line extending from the detector to the light source.

4. An optical absorption gas sensor according to claim 1, wherein the detector is in the form of an integrated device which has a first planar surface which forms the first surface of the detector assembly and which is adapted to measure light which falls onto one or more detection regions of the planar surface, normal to the planar surface and at a range of angles around the normal to the planar surface, wherein the light source is located within a volume defined by a prism which has the same cross-section as the first planar surface of the integrated device and which extends from a second surface of the integrated device perpendicular to the first planar surface of the integrated device.

5. An optical absorption gas sensor according to claim 1, wherein a first reflector and a second reflector are located on the internal wall and the majority of the light from the light source is reflected by both the first and second reflectors before it is incident on the detector.

6. An optical absorption gas sensor according to claim 1, wherein a collector is provided to direct the majority of the light from the light source onto a first reflector, the first reflector is configured to direct the majority of received light from the light source onto a second reflector and the second reflector is configured to direct the majority of light received from the light source via reflection by the first reflector onto the detector.

7. An optical absorption gas sensor according to claim 1, wherein the light which falls onto a first reflector is divergent, and a second reflector is concave and configured such that light reflected from the second reflector is less divergent than the light from the light source which is incident on the second reflector and such that light falling on the detector is predominantly convergent.

8. An optical absorption gas sensor according to claim 1, wherein the detector assembly extends from an inner edge of the chamber into the chamber.

9. An optical absorption gas sensor according to claim 8, wherein the first and second surfaces of the detector assembly are generally parallel with each other.

10. An optical absorption gas sensor according to claim 1, wherein the detector extends obliquely from the internal wall of the body of the sensor into the chamber such that the volume within the chamber on a first side of the detector is less than the volume within the chamber on a second side of the detector.

11. An optical absorption gas sensor according to claim 1, wherein the light source emits infra-red light.

12. An optical absorption gas sensor according to claim 1, wherein the sensor comprises a collector, located within the chamber, which has an interior reflective surface which directs light from the light source onto the first reflector through an output aperture of the collector.

13. An optical absorption gas sensor according to claim 1, wherein the sensor comprises a collector, and at least a portion of the collector has an interior reflective surface which takes the form of a part of a conic section rotated around an axis of rotation extending from the source to the first reflector.

14. An optical absorption gas sensor according to claim 13, wherein the interior reflective surface of the collector comprises at least a portion of an offset paraboloid or compound parabola.

15. An optical absorption gas sensor according to claim 13, wherein the interior reflective surface of the collector comprises a part-hemispherical portion and the light source is close to or intersects the centre of the part-hemispherical portion.

16. An optical absorption gas sensor according to claim 13, wherein the light-source is part of a light-emitting device which extends into the collector, through an aperture in the interior reflective surface of the collector.

17. An optical absorption gas sensor according to claim 16, wherein the light-emitting device extends into the collector through an aperture in the interior reflective surface of the collector in a direction which is at least partially rearwards, away from the output aperture.

18. An optical absorption gas sensor according to claim 1, wherein the distribution of light within the chamber is symmetric about a plane of symmetry which passes through the light source and the detector.

19. An optical absorption gas sensor according to claim 18, wherein the detector includes a measurement detector and a reference detector, and the measurement and reference detectors are located symmetrically on either side of the plane of symmetry, and the collector and first reflector are configured such that the distribution of light reflected from the surface of the first reflector is bifurcated.

20. An optical absorption gas sensor according to claim 1, wherein the majority of the light that reaches the detector from the light source travels in a substantially circumferential path over 180 degrees around a center point of a cross-section of the chamber.

21. An optical absorption gas sensor according to claim 20, wherein the cross-section is substantially circular.

22. An optical absorption gas sensor according to claim 1, wherein the range of angles is less than or equal to 90 degrees from a normal of the first surface.

23. An optical sensor comprising a light-emitting device including a light source, for use in generating light for the purposes of carrying out a measurement, and a collector having a reflective inner surface, an axis, and. an output aperture wherein the light-emitting device extends into the collector, through an aperture in the collector, other than parallel to the axis of the collector, the aperture through which the light emitting device extends is an aperture other than the output aperture, wherein the light-emitting device comprises an elongate light source which is neither parallel to, nor orthogonal to, the axis of the collector.

24. An optical sensor according to claim 23, wherein the light-emitting device has a base and a tip at the opposite end to the base, and the light source is located more than 50% of the distance from the base of the light-emitting device to the tip, wherein the light-emitting device extends into the collector in a direction which has a rearwards component, away from the output aperture.

25. An optical sensor comprising a light-emitting device which includes a light source, for use in generating light for the purpose of carrying out a measurement, and a collector which has a reflective inner surface disposed around the light source and an output aperture, wherein the collector comprises a part-spherical portion located on the side of the light source which is opposite to the output aperture, and the light source comprises the light emitting part of a luminescent filament and the collector has a longitudinal axis and the filament is elongate and orientated such that it is neither parallel to, nor orthogonal to, the longitudinal axis of the collector.

26. An optical sensor according to claim 25, wherein the radius of the part-spherical portion is less than ten times the length of the light-emitting part of a luminescent filament.

27. An optical absorption gas sensor comprising a light source and a detector, for measuring a light from the light source which has passed through a gas sample so that the concentration of an analyte gas can be established from the absorption of light by the analyte gas, wherein the sensor further comprises a collector having a reflective inner surface disposed around the light source, at least a portion of which is in the shape of at least a portion of a compound parabolic collector or offset paraboloid and the collector has a longitudinal axis and an elongate filament orientated such that it is neither parallel to, nor orthogonal to, the longitudinal axis of the collector.

* * * * *